US012224560B2

(12) United States Patent
Mantovan et al.

(10) Patent No.: US 12,224,560 B2
(45) Date of Patent: *Feb. 11, 2025

(54) IONIZATION DEVICE AND METHOD TO MANUFACTURE THEREOF

(71) Applicant: JONIX S.P.A., Tribano (IT)

(72) Inventors: Mauro Mantovan, Tribano (IT); Antonio Cecchi, Tribano (IT)

(73) Assignee: JONIX S.P.A., Tribano (IT)

( * ) Notice: Subject to any disclaimer, the term of this patent is extended or adjusted under 35 U.S.C. 154(b) by 793 days.

This patent is subject to a terminal disclaimer.

(21) Appl. No.: 17/409,151

(22) Filed: Aug. 23, 2021

(65) Prior Publication Data

US 2022/0054670 A1  Feb. 24, 2022

(30) Foreign Application Priority Data

Aug. 24, 2020 (IT) .................. 102020000020362

(51) Int. Cl.
*H01T 23/00* (2006.01)
*A61L 9/22* (2006.01)
*B05B 5/053* (2006.01)

(52) U.S. Cl.
CPC ............ *H01T 23/00* (2013.01); *A61L 9/22* (2013.01); *B05B 5/0535* (2013.01)

(58) Field of Classification Search
None
See application file for complete search history.

(56) References Cited

U.S. PATENT DOCUMENTS 3,350,602 A  * 10/1967  Germeshausen ......... H01T 1/00
                                                          315/176
2014/0079596 A1   3/2014  Gurman
2017/0333837 A1  11/2017  Bender et al.

FOREIGN PATENT DOCUMENTS

| EP | 3093073 A1 | 11/2016 |
| EP | 3120875 A1 | 1/2017 |
| EP | 3432691 A1 | 1/2019 |
| WO | 2012154727 A1 | 11/2012 |

OTHER PUBLICATIONS

Italian Search Report and Written Opinion dated May 6, 2021, in connection with International Application No. IT 202000020362, Applicant, Jonix S.P.A. (11 pages).
Italian Search Report and Written Opinion dated May 3, 2021, in connection with International Application No. IT 202000020359, Applicant, Jonix S.P.A. (13 pages).

* cited by examiner

*Primary Examiner* — Ashok Patel
(74) *Attorney, Agent, or Firm* — KLINTWORTH & ROZENBLAT IP LLP

(57) ABSTRACT

An ionising device is described comprising a tubular bulb of electrically insulating or dielectric material extending along a longitudinal reference axis and having the two opposite longitudinal terminal ends and open, a tubular cathode engaged in the bulb, a tubular anode fitted onto the bulb, a pair of covers coupled to a relative end of said bulb so as to hermetically close it, and a conductive electrode comprising a stem extending into said bulb, and a plurality of conductive crowns which are fitted onto the stem at predetermined distances from each other and are suitable to exert an elastic compression on the tubular cathode against the inner surface of the bulb.

11 Claims, 5 Drawing Sheets

IONIZATION DEVICE AND METHOD TO MANUFACTURE THEREOF

CROSS-REFERENCE TO RELATED APPLICATIONS

Figure 1:
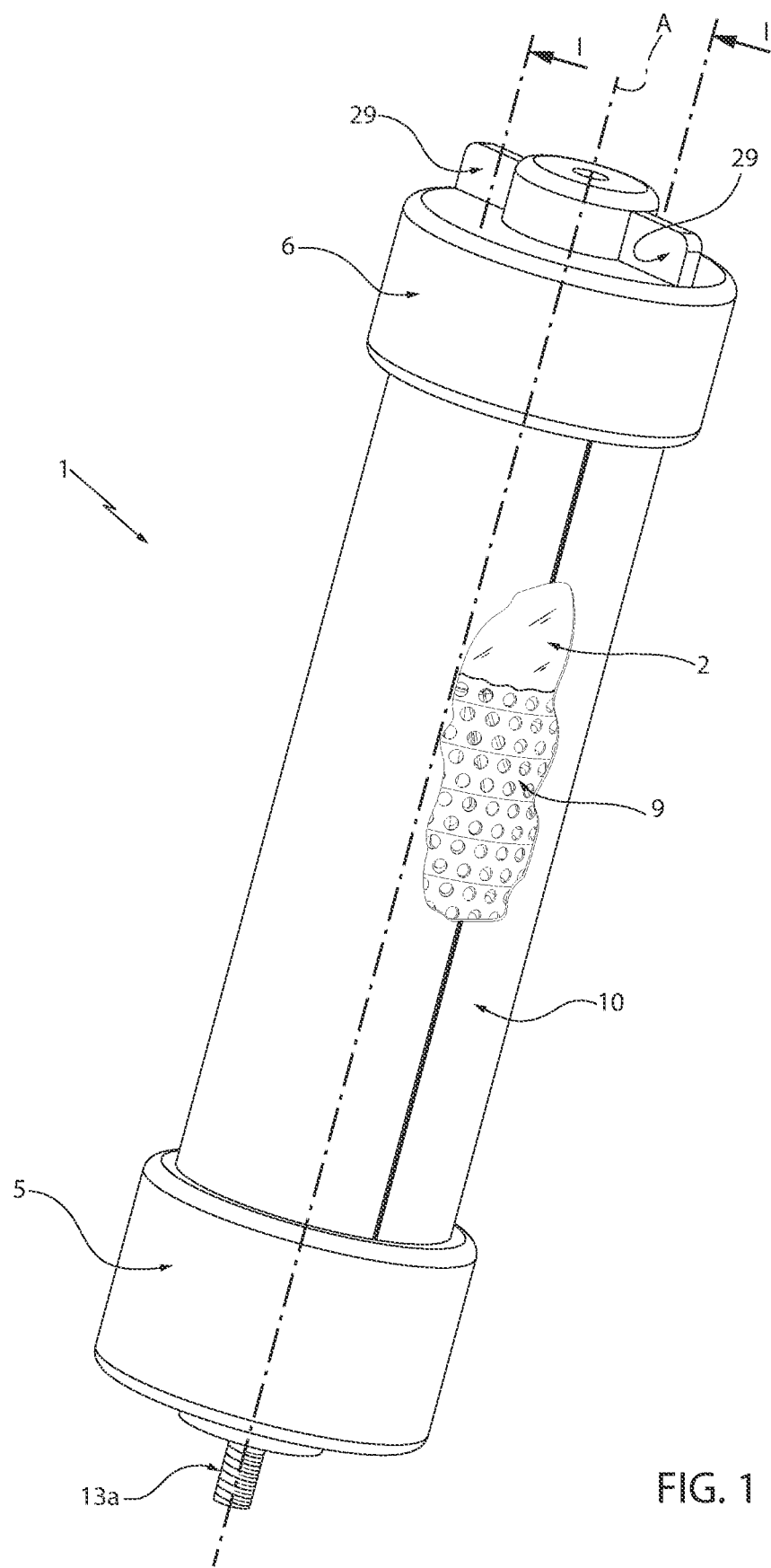

This patent application claims priority from Italian patent application no. 102020000020362 filed on Aug. 24, 2020, the entire disclosure of which is incorporated herein by reference.

FIELD OF THE ART

The present invention relates to an ionizing device and the related production method. In particular, the present invention relates to an ionizing device which, in use, purifies/sanitises a fluid, preferably a gaseous fluid, from contaminating particles such as, for example, viruses and bacteria, by implementing an ionizing process.

PRIOR ART

It is well known that there is a need to sanitise/purify the air in environments, especially closed ones, in order to reduce the risk of contamination of people and the environment by viruses and bacteria. So-called "cold plasma" ionizers have been developed for this purpose, which sanitize/purify the air by subjecting it to an ionizing process.

Some types of ionizing equipment are fitted with an ionizing device or generator also generally referred to as a bipolar ionizing tube or cylindrical capacitor, which is designed to generate an electric field that causes the corona effect when it is supplied with "high voltage", generally comprised between 1500 and 4000 volts, so as to ionize the air around it. The ionized air is then appropriately "mixed" with the fluids to remove pollutants/contaminating agents/particles from them.

An ionizing device used in the above ionizing equipment is described, for example, in U.S. Pat. No. 8,747,754 B2. The ionizing device described in the above patent comprises a tubular glass bulb, a cathode and an anode arranged inside and outside the bulb respectively.

The bulb has an elongated cylindrical shape and has an open longitudinal terminal end and a closed, roughly dome-shaped, opposite terminal end. The open terminal end is engaged in a seat of a cylindrical cover that forms the base of the ionizing device and houses an electrical power connector. The cover is firmly attached to the open end of the bulb by means of a series of layers of adhesive material which, after hardening, form hermetically sealed annular seals. The cathode and anode consist of two tubular metal jackets which are telescopically fitted inside and outside the bulb respectively, which acts as a dielectric.

The ionizing device also has a conductive electrode which is placed inside the bulb and electrically connects the electrical connector to the cathode. Specifically, the conductive electrode comprises a single crown which extends radially into the bulb so that it is in perimeter contact with the cathode, and a rod which is centrally placed in the bulb to support the conductive crown on its free end and electrically connects the latter to the electrical connector.

A technical problem with the ionizing device described above is that its production process is particularly complex and therefore has significant production costs.

In particular, a particularly critical and complex step of the process is the formation of the bulb and in particular the shaping of its terminal end during the operation of closing it. This step requires both a thermal softening operation of the vitreous matrix of the bulb with consequent non-negligible waiting times, and manual intervention to shape the closing portion of the dome-shaped end.

This step is also particularly critical as, in addition to being subject to dimensional inaccuracies in the formation of the bulb, it is exposed to localized thermal alterations that mechanically weaken the closed end of the bulb with all the consequences that this entails in terms of exposure to bulb breakage in the event of accidental impact.

Another critical part of the process is the coupling of the bulb with the cover and the mutual fixing of the two. Firstly, the operation of mounting the cover on the bulb is exposed to mutual positioning errors between the bulb, the conductive electrode and the conductive crown. In particular, at this stage, a misalignment of the conductive electrode and/or incorrect positioning of the crown with respect to the bulb can affect the electrical parameters characterizing the capacitor and lead to malfunctioning and/or impair its efficiency. For example, incorrect positioning of the crown causes the cathode to adhere imperfectly to the bulb and leads to an increase in the thickness of the dielectric between the cathode and the anode, which alters the correct functioning of the capacitor.

In addition, after inserting the cover on the bulb and applying the fixing adhesive, it is necessary to wait for it to harden (polymerisation). This operation is particularly time-consuming and therefore has a significant impact on the production time of the ionizing device. In addition, incorrect gluing can impair the hermetic seal of the open end of the bulb. If the bulb is not airtight, oxygen can enter the bulb and oxidise the conductive electrode and/or cathode, thereby impairing the correct functioning of the ionizing device.

Lastly, fixing the cover to the bulb using glue requires the glue to be removed during maintenance of the ionizing device, an operation that is particularly critical in terms of both time and the risk of damage to the bulb, as well as the application of new glue to restore the device.

DISCLOSURE OF THE INVENTION

The aim of the present invention is therefore to produce an ionizing device which overcomes the drawbacks described above.

According to the present invention, an ionizing device, an ionizing apparatus and a method for producing the ionizing device are implemented as disclosed in the appended claims.

BRIEF DESCRIPTION OF THE FIGURES BRIEF DESCRIPTION OF THE DRAWINGS

Figure 2:
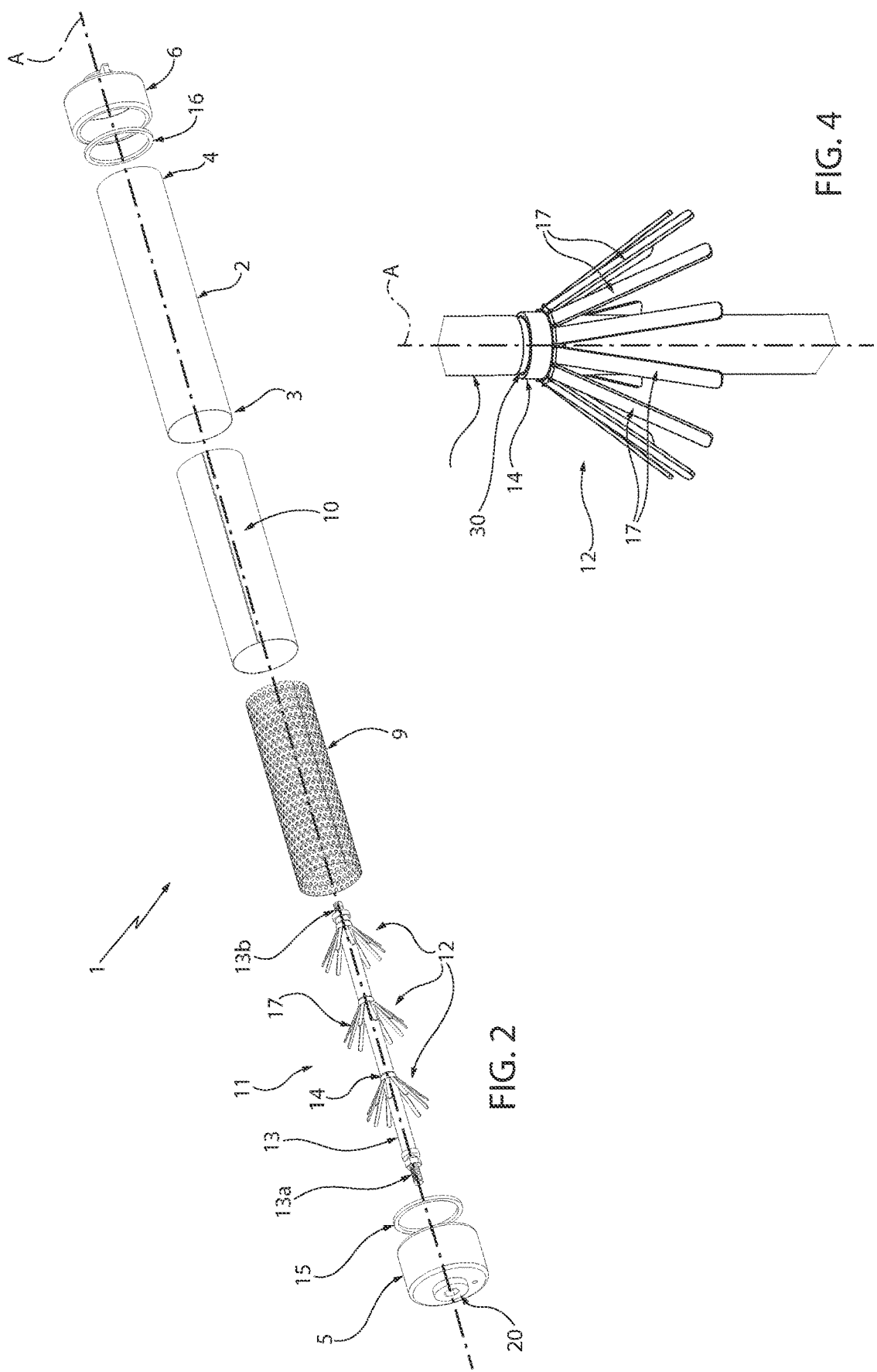
Figure 3:
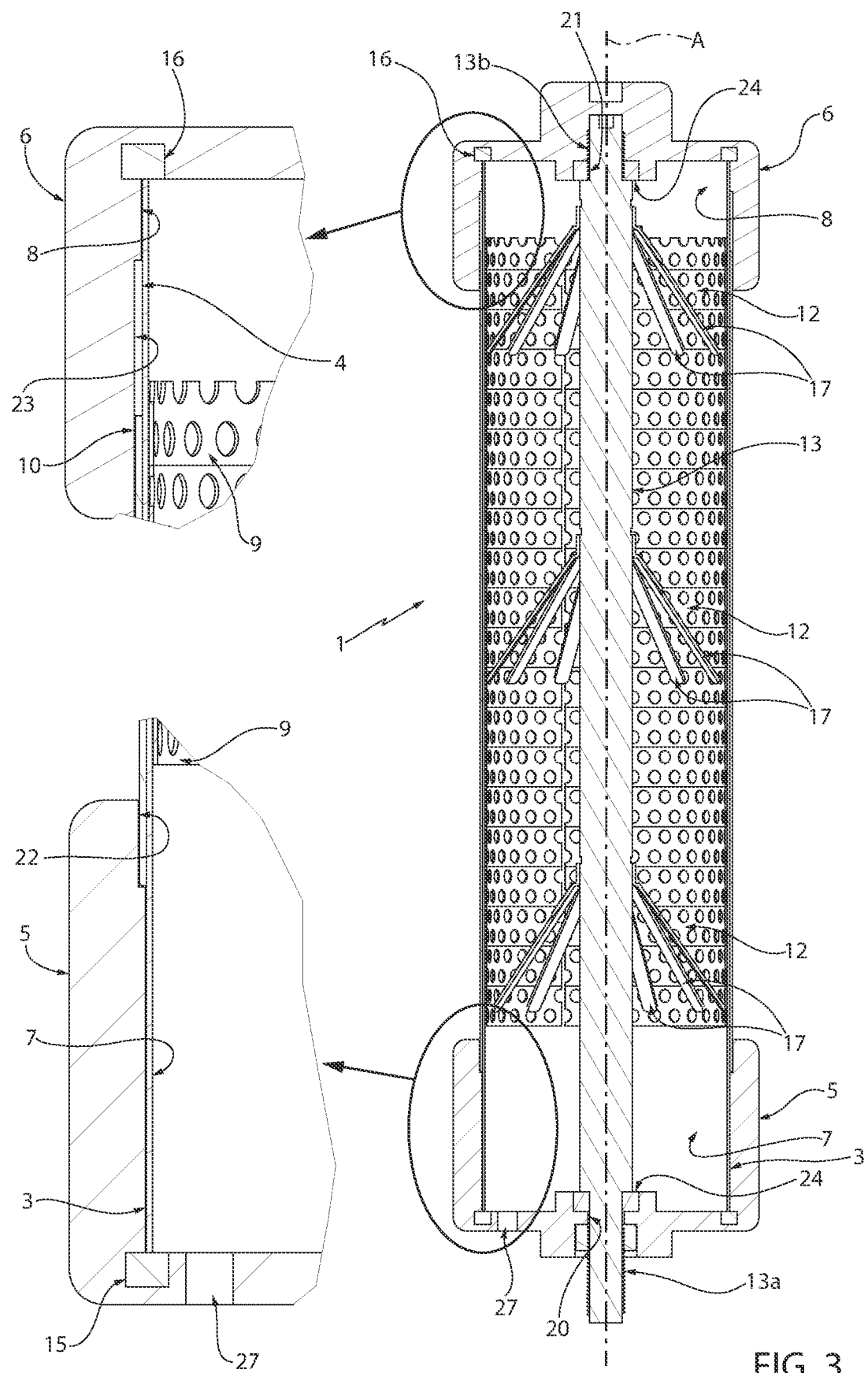
Figure 6:
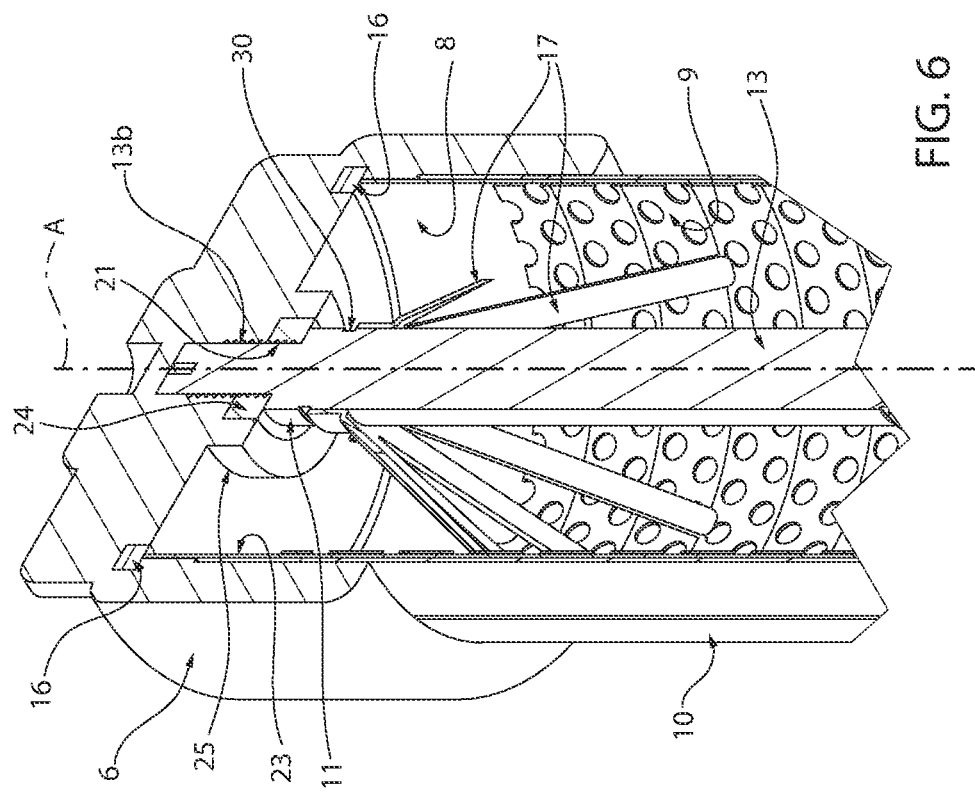
Figure 5:
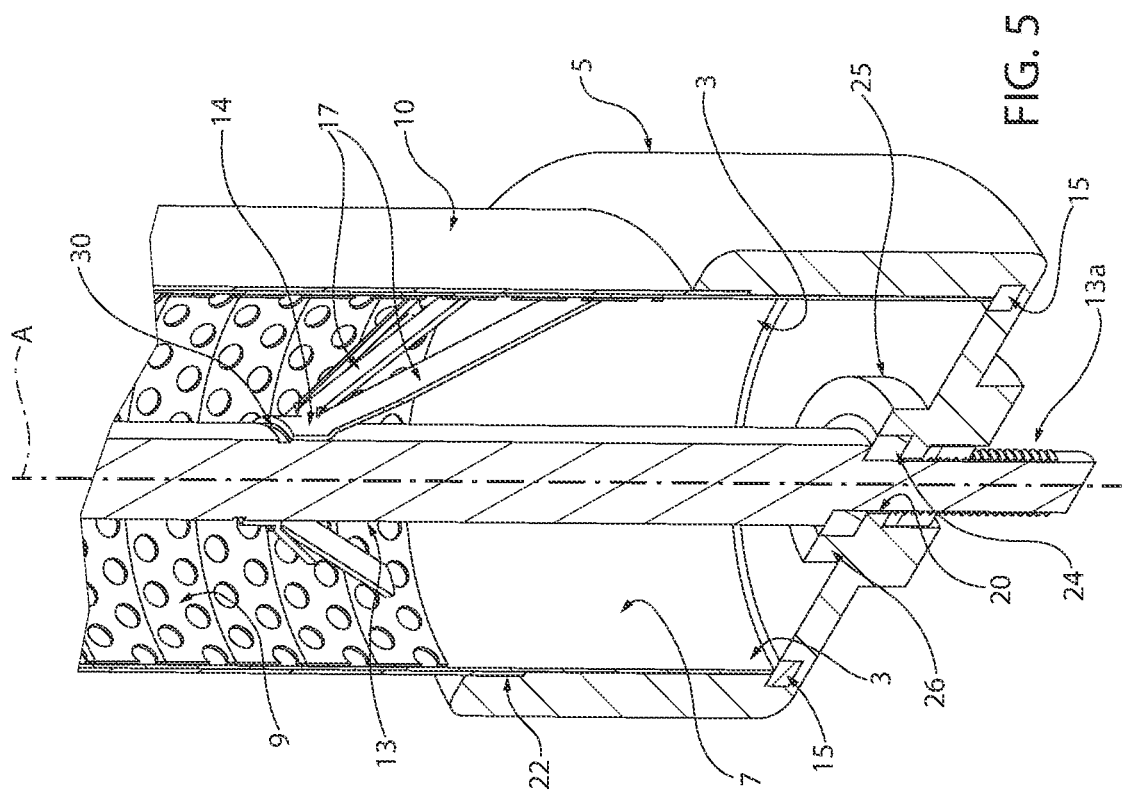
Figure 7:
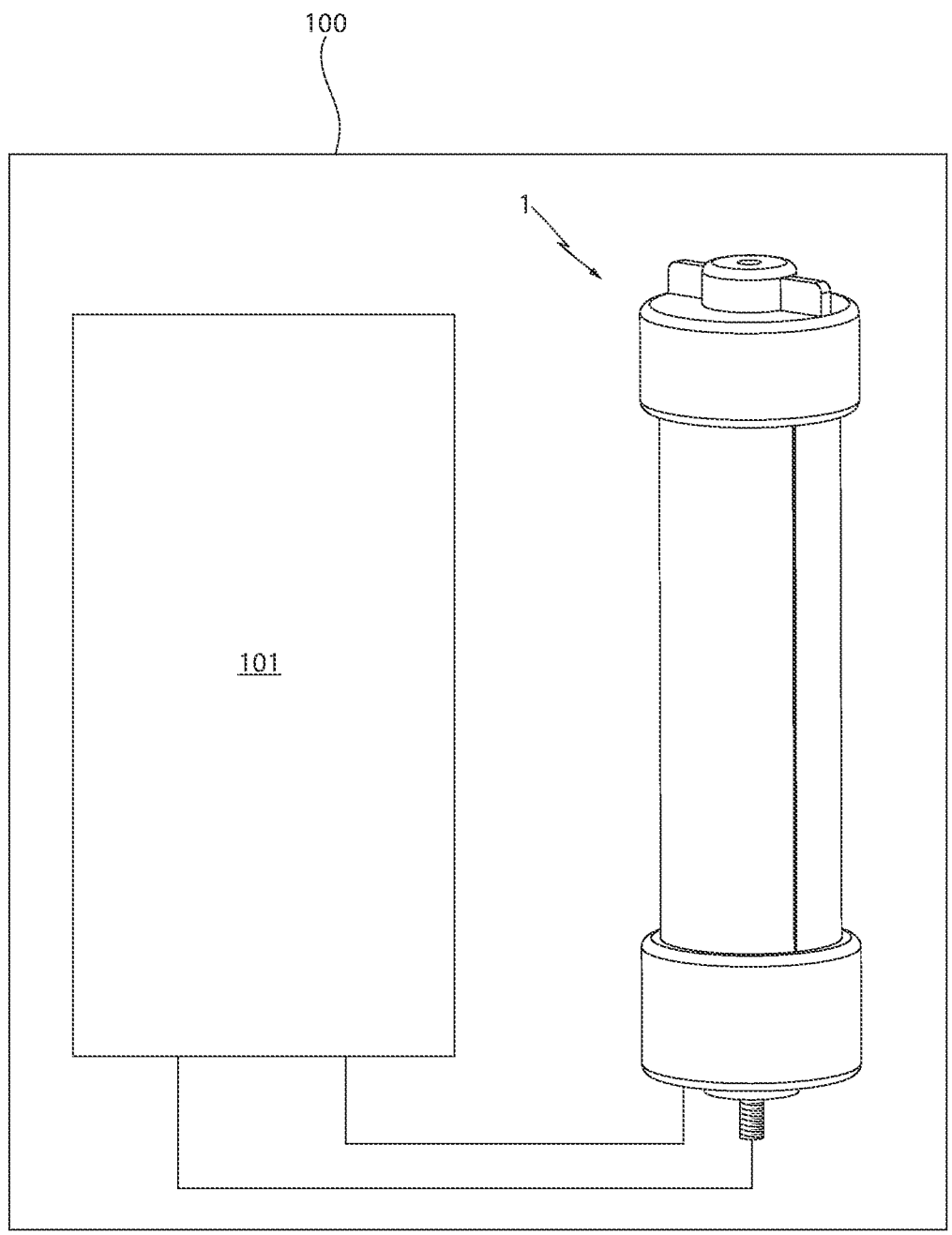

The invention is described below with reference to the accompanying drawings, wherein:

FIG. 1 is a perspective view, with parts removed for clarity, of an ionizing device realized according to the dictates of the present invention, FIG. 2 is an exploded view of the ionizing device shown in FIG. 1, FIG. 3 is the I-I section of the ionizing device shown in FIG. 1, FIG. 4 is a perspective view, on an enlarged scale and with parts removed for clarity, of a detail of a conductive electrode comprised in the ionizing device made according to the present invention, and FIGS. 5 and 6 are enlarged cross-sectional views of the ionizing device shown in FIG. 1, FIG. 7 is a schematic view of an ionizing apparatus provided with an ionizing device realized according to the dictates of the present invention.

PREFERRED EMBODIMENTS OF THE INVENTION

In FIG. 1, the number 1 denotes a "cold plasma" generator or ionizing device, which is designed to ionise a fluid in such a way as to remove/destroy, by oxidative effect, predetermined contaminating particles. For example, the predetermined contaminating particles according to the present invention may comprise biological or micro-organic particles (bacteria, viruses, moulds, by-products thereof e.g., endotoxins) as well as chemical pollutants present in the fluid itself, and/or volatile organic substances or the like.

In the following discussion, explicit reference will be made to the ionisation of a gaseous fluid corresponding to air. However, it is understood that the present invention is not limited to a gaseous fluid but can also be applied to purify a liquid fluid.

According to a preferred embodiment shown in FIGS. 1-5, the ionizing device 1 has approximately the structure of a cylindrical ionising capacitor and comprises a bulb 2, which has a tubular shape and extends approximately straight along a reference axis A. The bulb 2 is made of electrically insulating or dielectric material, preferably glass or the like. The bulb 2 has an elongated, approximately rectilinear shape extending along the axis A and has both opposite axial terminal ends, denoted 3 and 4, open. In the example shown, the bulb 2 has a circular cross-section to the axis A and the two terminal ends 3 and 4 are defined by two circular edges coaxial to the axis A.

With reference to FIGS. 1-5, the ionizing device 1 further comprises two covers 5 and 6 which are permanently coupled to the two terminal ends 3 and 4 respectively of the bulb 2 in such a way that they are hermetically sealed. The covers 5 and 6 consist of two cup-shaped bodies made of electrically insulating material, e.g., polymeric material (plastic), and have respective internal seats 7 and 8 into which the longitudinal terminal ends 3 and 4 of the bulb 2 are respectively engaged.

The Applicant has found that the use of a tubular bulb 2 with both terminal ends 3 and 4 being open and the use of two opposing closing covers 5 and 6 positioned on the two open terminal ends 3 and 4 so as to close them, has the technical effect of eliminating the criticality associated with the use of a bulb with one closed end. In fact, the use of a bulb 2 open at both terminal ends 3 and 4 makes it possible, on the one hand, to increase its strength as it eliminates the intrinsic fragility caused by the closed end and, on the other hand, it reduces the time required to make the bulb as it is possible to make transversal cuts to the axis A on a rectilinear tubular body in order to make the two open terminal ends 3 and 4 that delimit the bulb 2, completely automatically, i.e. without any manual intervention. In addition, the closing operation of bulb 2 involves a quick operation of inserting the two covers 5 and 6 on the ends 3 and 4 of bulb 2, an operation that can also be performed, thanks to its simplicity, by an automated system.

According to the preferred embodiment, the internal seats 7 and 8 of the covers 5 and 6 have an approximately cylindrical shape which is complementary to the outer shape of the terminal ends 3 and 4 of the bulb 2 so as to accommodate them internally. Preferably, the axial length of a seat of a cover (the cover 6 in FIG. 3) measured along the axis A is greater than the axial length of the seat of the other cover (the cover 5 in FIG. 3).

According to the preferred embodiment shown in FIGS. 3 and 4, the annular edges of the two terminal ends 3 and 4 of the bulb 2 are arranged in abutment against the bottom walls of the relevant seats 7 and 8, orthogonal to the axis A, by means of the interposition of relevant annular gaskets 15 and 16. Preferably, the annular gaskets 15 and 16 can be conveniently made from an elastomeric material, and can be accommodated in respective annular grooves formed on the bottom walls of the seats 7 and 8. Conveniently, the annular gaskets 15 and 16 can be made on the relative covers 5 and 6 by a process of co-moulding the covers 5 and 6 themselves.

With reference to FIGS. 1-5, the ionizing device 1 further comprises a cathode 9 and an anode 10 arranged inside and outside the bulb 2 respectively. According to a preferred exemplary embodiment shown in FIGS. 1-5, the cathode 9 and the anode 10 have tubular shapes. Preferably, the cathode 9 and the anode 10 comprise respective thin plates which have a circular cross-sectional area to the axis A and form the two electrical armatures of the capacitor between which the bulb 2 is arranged defining the inner cylindrical dielectric layer.

In the example shown, the cathode 9 comprises a perforated plate which has the outer cylindrical surface approximately resting on the inner cylindrical surface of the bulb 2. Conveniently, the cathode 9 is telescopically fitted into the bulb 2 in a stable but easily removable (detachable) manner so that it can be axially pulled out therefrom along the axis A.

In the example shown, the anode 10 comprises a sheet (solid i.e., not perforated) having its inner cylindrical surface approximately resting on the outer cylindrical surface of the bulb 2. Conveniently, the anode 10 is telescopically fitted onto the bulb 2 in such a way that it can be easily pulled out therefrom along the axis A.

The cathode 9 and the anode 10 may be made of an electrically conductive material, preferably metal, such as aluminium and/or steel or the like.

It is understood that the present invention is not limited to the use of a cathode 9 provided with a perforated tubular sheet and/or an anode 10 provided with a tubular sheet but may include other embodiments. For example, according to an alternative embodiment (not illustrated), the cathode 9 may be formed by a tubular mesh, or by a layer of electrically conductive material stably deposited on the inner tubular surface of the bulb 2.

Furthermore, according to an alternative embodiment (not illustrated) the anode 10 may be formed by a wire mesh or perforated sheet or a layer of electrically conductive material stably deposited on the outer tubular surface of the bulb 2.

Preferably, the opposite axial ends of the tubular anode 10 are conveniently engaged in relative self-centring annular recesses 22 and 23 which are formed on the end part of the cylindrical inner wall of the seats 7 and 8 parallel to the axis A. Preferably, the self-centring annular recesses 22 and 23 extend from the annular edges of the cup-shaped bodies of the covers 5 and 6 towards the respective end wall for predetermined axial lengths and have an inner diameter that corresponds approximately to the outer diameter of the anode 10. The remaining part of the seats 7 and 8 comprised between the relative end wall and the corresponding annular recesses 22 and 23 has an inner diameter less than the outer diameter approximately equal to the outer diameter of the bulb 2 so as to accommodate the latter.

The technical effect of the annular recesses 22 and 23 is to self-centre the anode 10 on the covers 5 and 6 during assembly and to simplify the construction of the ionizing device 1.

Preferably, the axial lengths of the self-centring annular recesses 22 and 23 measured along the axis A may be different from each other. According to a preferred embodiment shown in FIG. 3, the annular recess 23 has a conveniently greater axial length than the annular recess 22. It is understood that according to an alternative embodiment the lengths of the annular recesses 22 and 23 may be inverted, i.e., the axial length of the annular recess 23 may be greater than the axial length of the annular recess 22.

The difference in axial length of the two recesses 22 and 23 has the technical effect of obtaining a tolerance or axial clearance which allows the axial position of the anode 10 to be adjusted appreciably in relation to the bulb 2 and/or the cathode 9 during assembly. Furthermore, the greater length of the recess in one of the two covers simplifies the operation of decoupling the anode 10 from the bulb 2 as it requires the decoupling of a single cover provided with the recess itself.

The ionizing device 1 further comprises a conductive electrode 11 made of an electrically conductive material, for example metal, which is arranged within the bulb 2 and the cathode 9, and is shaped to electrically power the cathode 9.

According to a preferred embodiment shown in FIGS. 1-5, the conductive electrode 11 comprises a rod or stem 13 that extends centrally in the bulb 2 along the axis A and a plurality of conductive crowns 12 that are mounted on the stem 13 at predetermined axial positions spaced apart from each other along the axis A. The conductive crowns 12 have an approximately "flower" shape whose radial plate-like portions approximately define petals extending transversely to the axis A and have their distal ends in contact with the inner surface of the cathode 9.

According to a preferred exemplary embodiment shown in FIG. 3, the conductive crowns 12 are equidistant from each other along the axis A. Preferably, the stem 13 is rectilinear and has an approximately circular cross-sectional area to the axis A.

The Applicant has found that the use of a series of mutually spaced conductive crowns 12 along the axis A has the technical effect of improving the uniform distribution of electrical charges in the armature of the cathode 9 of the capacitor by the conductive electrode 11. A further technical effect achieved by the use of a series of mutually spaced conductive crowns 12 along the support bar 13 is to ensure increased adhesion of the cathode armature 9 against the inner surface of the bulb 2. In particular, the Applicant has found that the use of a series of axially spaced conductive crowns 12 enables localised radial forces to be exerted which push the cathode 9 against the bulb 2 at several points along the axis A and thus ensure electrical coupling between the electrical armature of the cathode 9 and the dielectric layer of the capacitor constituted by the bulb 2. This makes it possible to advantageously overcome the technical problem present in state-of-the-art ionizing devices, which consists of the formation of zones of imperfect electrical adhesion between cathode 9 and bulb 2. The presence of non-adhering zones results in an increase in dielectric (air gap) and consequently a localised deterioration in the performance of the cylindrical ionizing capacitor.

According to a preferred embodiment shown in FIGS. 2-6, the conductive crowns 12 are centrally provided with respective annular collars 14 which are fitted onto the support bar 13 and from which radially cantilevered portions formed by approximately petal-shaped tabs 17 extend.

According to a preferred exemplary embodiment shown in FIG. 3, the tabs 17 are inclined with respect to the axis A and are arranged in the cathode 9 in such a way that they are elastically open in support against the inner surface of the cathode 9.

The Applicant has found that a technical effect of the annular collars 14 is to increase the electrical contact between the conductive crown 12 and the stem 13 and to reduce the formation of voltage spikes and localized currents. Another technical effect of the annular collars 14 is also to ensure the correct positioning coaxial to the axis A of the conductive crowns 12 within the cathode 9.

In order to advantageously ensure the correct axial positioning of the conductive crowns 12 along the stem 13, a series of annular grooves 30 are formed which are axially spaced along the axis A with respect to each other on the basis of the positions associated with the relative conductive crowns 12, and are shaped so as to accommodate respective annular overhangs (not illustrated) present in the inner wall of the collars 14 of the conductive crowns 12 themselves.

According to a preferred embodiment shown in FIGS. 3, 5 and 6, the stem 13 has opposite ends 13a and 13b which are respectively stably coupled to the covers 5 and 6 in such a way as to keep them axially engaged in the bulb 2.

According to a preferred exemplary embodiment shown in FIG. 3, the opposite ends 13a and 13b of the support bar 13 are externally threaded and are screwed into respective internally threaded openings 20 and 21 centrally formed on the bottom walls of the seats 7 and 8 coaxial to the axis A.

The Applicant has found that, the use of the stem 13 with axial ends 13a and 13b connected to the covers 5 and 6 has the technical effect of simplifying the assembly of the covers 5 and 6 on the bulb 2 as it helps to ensure the centring of the conductive electrode 11 with respect to the bulb 2, and vice versa. Another technical effect is to ensure that the two open terminal ends 3 and 4 of bulb 2 are hermetically sealed without the use of adhesive fixing materials. In fact, screwing the covers 5 and 6 onto the ends 13a and 13b of the stem 13 results in an axial clamping of the covers 5 and 6 against the bulb 2 which causes a controlled compression of the annular edges of the ends 3 and 4 against the corresponding annular gaskets 15 and 16 which hermetically seal the ends 3 and 4 themselves.

The stem 13 with its threaded axial ends 13a and 13b screwed onto the covers is conveniently designed to allow the covers 5 and 6 to be attached/locked to the ends 3 and 4 of the bulb 2 in such a way as to close them.

The stem 13 with threaded axial ends 13a and 13b screwed onto the covers is conveniently adapted in use to allow the release of the covers 5 and 6 at the ends 3 and 4 of the bulb 2 so as to open them to allow the disassembly of one or more parts of the ionizing device 1 in case of maintenance.

According to the preferred embodiment shown in FIGS. 1-5, annular inserts 24 are fitted on the threaded ends 13a and 13b, which are housed approximately in the openings 20 and 21. Preferably on the bottom walls of the covers 5 and 6 in correspondence with the openings 20 and 21, there may be annular shoulders 25 coaxial to the axis A which internally delimit annular seats 26 in which the annular inserts 24 are housed. Preferably the annular inserts 24 can be made of silicone or a similar material.

The technical effect of the annular inserts 24 is to help ensure the hermetic seal of the covers 5 and 6 at the openings 20 and 21 engaged by the stem 13 of the conductive electrode 11.

According to a preferred embodiment shown in FIGS. 1-5, one of the openings, opening 20 comprises a through hole, which is formed on the bottom wall of the cover 5 so as to be coaxial to the axis A and is crossed by the end 13*a* of the support bar 13. The end 13*a* may be suitably sized so as to axially cross the bottom wall of the cover 5 so as to protrude outside the cover so as to form an external electrical connector for supplying the cathode 9.

Preferably, the end 13*a* may be connected to the lid 5 by means of a threaded nut engaged/stably housed in an enlarged end portion of the opening 20 formed on the outer surface of the bottom wall of the cover 5.

It is understood that according to one embodiment, the hole 20 of the cover 5 may be internally threaded to be connected with the threaded end 13*a* of the stem 13.

According to a preferred embodiment shown in FIGS. 1-5, the opening 21 may comprise an internally threaded blind hole that is formed on the back wall of the cover 6. Conveniently, the face of the end 13*b* of the support bar 13 orthogonal to the axis A can be shaped in complementary way to the end of a tool so that the stem 13 can be easily screwed/unscrewed with the opposite end 3*a* onto the cover 5 during assembly.

In accordance with a preferred embodiment, at least one of the two covers 5 and 6 may be provided with fins 29 to facilitate the screwing/unscrewing of the cover during assembly. In the illustrated example, the fins 29 are arranged on the outer surface of the bottom wall of the cover 6 and extend approximately radially to the axis A, starting from a central cylindrical portion projecting coaxially to the axis A. According to an additional or alternative embodiment, the fins 29 may be shaped in the form of a "J".

The ionizing device 1 described above is designed to be comprised in an ionizing apparatus for sanitising/purifying the fluid. FIG. 7 shows schematically by way of non-limiting example an ionizing apparatus 100 comprising the ionizing device 1 of the type described above. The ionizing apparatus 100 further comprises an electronic control system 101, which is electrically connected to the ionizing device and is configured to supply a high voltage having a predetermined value thereto. It is understood that, additionally or alternatively, the ionizing apparatus 100 may comprise a plurality of ionizing devices 1.

According to a possible embodiment, the electronic control system 101 may be conveniently produced as described in Italian patent no. 1429908 and/or European invention patent no. EP 3 093 073 B1, the contents (description and tables) of which are hereby fully incorporated for reference purposes.

The method for producing the ionizing device 1 comprises arranging the bulb 2, arranging the anode 10, arranging the cathode 9, arranging the stem 13, arranging the conductive crowns 13 and arranging the covers 5 and 6.

The bulb 2 may be conveniently obtained by arranging a straight tubular element made of electrically insulating or dielectric material, e.g., glass, extending along an axis, and making cuts in the tubular element in planes orthogonal to the axis on the basis of the length of the bulb 2 to be obtained.

The method further comprises the following steps: mounting the conductive crowns 12 on the stem 13 in positions axially distant from each other, telescopically engaging the cathode 9 inside the bulb 2, mounting the stem 13 in the cover 5 by screwing the end 13*a* into the nut present in the opening 20, engaging the conductive electrode 11 in the cathode 9 pre-assembled in the bulb 2 so that the tabs 17 of the conductive crowns 12 adhere elastically to the internal surface of the cathode 9, coupling the cover 5 to the end 3 of the bulb 2 until the end 3 of the bulb 2 is positioned in the seat 7 in abutment against the annular gasket 15 and the bottom wall, fitting the anode 10 onto the bulb 2 so as to engage its end in the annular recess 22 of the cover 5, screwing the stem 3 so as to compress the annular insert 24 in the opening 20, engaging the cover 6 on the end 4 of the bulb 2 with the opening 21 engaged on the end 13*b* of the stem 13 and screw the cover 6 around the stem 13 so as to cause the compression of the gasket 15 by the end 4 of the bulb 2.

The method further preferably but not necessarily comprises the step of extracting air from the bulb 2 preferably through a through hole 27 arranged on the bottom wall of the cover 5 so as to create a vacuum, injecting an inert gas into the bulb 2, and hermetically sealing the through hole 27. The use of inert gas in combination with the hermetic sealing of the bulb 2 prevents oxidation of the conductive electrode 11 and/or cathode 9.

It should be noted that the ionizing device 1 can be conveniently disassembled by simply unscrewing the covers from the stem and uncoupling them from the bulb 2 and then removing the anode, cathode and conductive electrode from the bulb.

The ionizing device 1 described above has at least the following advantages.

The use of the tubular bulb with both (open) terminal ends being closed by removable covers makes it possible to: simplify the production process and on the other hand, reduce dimensional inaccuracies, and increase the strength of the ionizing device.

The ionizing device is also easy to assemble and has a high degree of hermetic sealing without the use of adhesives, thanks to the presence of the annular grooves in the covers and the central threaded openings in the covers themselves to which the conductive electrode is coupled.

The use of the series of conductive crowns also ensures high adhesion of the cathode to the bulb as well as improved distribution of electrical charges on the cathode.

Finally, it is clear that modifications and variations may be made to the ionizing device and the method of producing the ionizing device and/or the ionizing apparatus described and illustrated herein without departing from the scope of protection of the present invention in accordance with the appended claims.

For example, according to one embodiment (not illustrated), the ionizing device may envisage the use of a bulb with a single opening closed by a relative cover. In this case, the conductive electrode can be connected with one end in the cover extending into the bulb and the other end opposite the stem free and suspended, i.e., not connected to the bulb.

The invention claimed is:

1. Ionizing device (1) adapted to ionize a fluid for removing/breaking down from the fluid contaminating particles,
characterized in comprising:
a tubular bulb (2) made from an electrically insulating or a dielectric material, extending along a longitudinal reference axis (A) and presenting at least one longitudinal open terminal end (3)(4);
a tubular cathode (9) inserted into the bulb (2),
a tubular anode (10) fit onto the bulb (2),
at least one cover (5)(6) coupled to the open terminal end (3)(4) of the bulb (2) so as to hermetically close the open terminal end (3)(4);
a conducting electrode (11) comprising a stem (13) extending within said bulb (2) along said longitudinal reference axis (A) and a plurality of conductive crowns (12) fitted onto said stem (13) at pre-established distances one from another along said reference axis (A) and which are adapted to exert an elastic radial compression onto said tubular cathode (9) against the internal surface of said bulb (2) at a plurality of points axially distanced along said reference axis (A), wherein said bulb (2) has two opposite longitudinal open terminal ends (3)(4), the ionizing device (1) further comprises two covers (5) (6) coupled to said opposite longitudinal terminal ends (3)(4) of said bulb (2) so as to close them, and wherein said conducting electrode (11) is designed for mechanically connecting said covers (5) (6) between one another for exerting a traction onto said covers (5) one towards the other along the axis (A) so as to compress both against the annular edges of said terminal ends (3)(4) of said bulb (2) so as to hermetically close these.

2. Ionizing device according to claim 1, wherein said conductive crowns (12) comprise respective annular collars (14) fitted onto said stem (13) and a plurality of tabs (17), which radially extend in a cantilevered manner from said annular collar (11) towards said cathode (9) and resting on the same.

3. Ionizing device according to claim 1, wherein said stem (13) presents opposite longitudinal ends (13a) (13b) mechanically coupled to said covers (5) (6).

4. Ionizing device according to claim 3, wherein the opposing longitudinal ends (13a)(13b) are coupled to said covers (5)(6) through threaded means adapted to allow to lock and unlock said covers (5)(6) onto said terminal ends (3)(4) of the bulb (2) in such a manner to respectively close and open the terminal ends (3)(4) of the bulb (2).

5. Ionizing apparatus comprising at least one ionizing device (1) according to claim 1 and an electronic control system (101), which is electrically connected to the ionizing device (1) and which is configured to power the ionizing device (1) with a pre-established high voltage power supply.

6. Ionizing device according to claim 1, further including annular gaskets (15) (16), wherein said covers (5) (6) comprise cup bodies, wherein the annular gaskets (15) (16) are interposed between said terminal ends (3)(4) of said bulb (2) and the cup bodies of the covers (5) (6), respectively, and are arranged in abutment with bottom walls of said cup bodies.

7. Ionizing device according to claim 1, wherein said covers (5)(6) are provided each with a respective internal seat (5)(6) within which are inserted a respective terminal end (3)(4) of said bulb (2) so as to hermetically close the respective terminal end (3)(4).

8. Ionizing device according to claim 7, wherein said covers (5)(6) are provided with relative self-centering annular grooves (18)(19), which are obtained within the respective internal seats (7)(8) and which are dimensioned for only receiving the longitudinal ends of said anode (10).

9. Ionizing device according to claim 1, comprising an inert gas within the inside of said bulb (2).

10. Method of producing an ionizing device characterized in comprising the following steps:

providing a tubular bulb (2) made from an electrically insulating or a dielectric material, extending along a longitudinal reference axis (A) and having at least one longitudinal open terminal end (3)(4);

engaging a tubular cathode (9) onto an internal surface of said bulb (2);

fitting a tubular anode (10) onto the external surface of said bulb (2);

provide a conducting electrode (11) which comprises a stem (13) and a plurality of conductive crowns (12), which are fit onto said stem (13) at pre-established distances one after the other along the longitudinal axis of said stem (13);

positioning said conductive electrode (11) within said bulb (2) so as to arrange said conductive crowns (12) into contact with the internal surface of said tubular cathode (9) in such a manner so as to exert an elastic compression onto said tubular cathode (9) against the internal surface of said bulb (2) at a plurality of points axially distanced between one another along said axis (A), hermetically closing said at least one terminal end (3)(4) od said bulb (2) through a relative closing cover (5)(6), wherein:

said bulb (2) has two opposite longitudinal open terminal ends (3)(4), the method comprising the step of coupling the two covers (5)(6) onto said opposing terminal ends (3)(4) of said bulb (2) so as to close the terminal ends (3)(4);

the method further comprises the step of mechanically connecting said covers (5)(6) between one another through said conducting electrode (11) so as to exert a compression onto said covers (5)(6) along said axis (A) against the edges of said covers (5)(6) of said bulb (2) so as to hermetically closing these.

11. Method according to claim 10 comprising the steps of:

creating a vacuum inside of said hermetically closed bulb (2);

introducing an inert gas into said bulb (2).

* * * * *